United States Patent [19]
Gustafsson et al.

[11] Patent Number: 6,120,787
[45] Date of Patent: Sep. 19, 2000

[54] SUSTAINED RELEASE PARTICLES

[75] Inventors: Nils-Ove Gustafsson, Löddeköpinge; Timo Laakso, Höllviken; Peter Fyhr, Bjarred; Monica Jönsson, Bara, all of Sweden

[73] Assignee: Biogram AB, Malmö, Sweden

[21] Appl. No.: 09/051,709

[22] PCT Filed: Sep. 3, 1996

[86] PCT No.: PCT/SE96/01091

§ 371 Date: Apr. 17, 1998

§ 102(e) Date: Apr. 17, 1998

[87] PCT Pub. No.: WO97/14408

PCT Pub. Date: Apr. 24, 1997

[30] Foreign Application Priority Data

Oct. 19, 1995 [SE] Sweden .................................. 9503672

[51] Int. Cl.⁷ ...................................................... A61F 2/00
[52] U.S. Cl. .......................... 424/426; 424/489; 424/497; 424/486; 424/461; 424/468; 424/426; 424/490
[58] Field of Search ................................. 424/426, 489, 424/490, 491, 488, 402.21, 484, 485, 486

[56] References Cited

U.S. PATENT DOCUMENTS

| | | |
|---|---|---|
| 4,384,975 | 5/1983 | Fong . |
| 4,479,911 | 10/1984 | Fong . |
| 4,568,559 | 2/1986 | Nuwayser et al. . |
| 4,623,588 | 11/1986 | Nuwayser et al. . |
| 4,637,905 | 1/1987 | Gardner . |
| 4,666,704 | 5/1987 | Shalati et al. . |
| 4,677,191 | 6/1987 | Tanaka et al. . |
| 4,822,535 | 4/1989 | Ekman et al. . |
| 4,835,139 | 5/1989 | Tice et al. . |
| 4,849,228 | 7/1989 | Yamamoto et al. . |
| 5,275,819 | 1/1994 | Amer et al. . |
| 5,288,502 | 2/1994 | Mc Ginity et al. ............ 424/484 |
| 5,417,982 | 5/1995 | Modi . |
| 5,679,377 | 10/1997 | Bernstein et al. ............ 424/491 |

FOREIGN PATENT DOCUMENTS

| | | |
|---|---|---|
| 0535937 A1 | 4/1993 | European Pat. Off. . |
| 88/07870 | 10/1988 | WIPO . |
| 90/13780 | 11/1990 | WIPO . |
| 94/12158 | 6/1994 | WIPO . |

*Primary Examiner*—Thurman K. Page
*Assistant Examiner*—William E. Benston, Jr.
*Attorney, Agent, or Firm*—Burns, Doane, Swecker & Mathis, L.L.P.

[57] ABSTRACT

A method of preparing parenterally administrable sustained release microparticles, which comprises preparing core particles in an aqueous medium that is essentially free from organic solvent, a biologically active substance being entrapped therein during or after said preparation, drying the core particles and coating the same with a release-controlling polymer by air suspension technique so as to create a shell on the core particles without any detrimental exposure of the active substance to organic solvent. Microparticles obtainable by such a method also are provided.

32 Claims, 5 Drawing Sheets

SUSTAINED RELEASE PARTICLES

This application is a 371 of PCT/SE96/01091 filed Sep. 3, 1996.

TECHNICAL FIELD

The present invention is within the field of sustained release particles for parenteral administration of biologically active substances, especially drugs. More specifically it relates to a new preparation method for such particles containing a biologically active substance as well as to new sustained release particles obtainable thereby.

BACKGROUND OF THE INVENTION

Many drugs have to be administered by injection since they are either degraded or absorbed inefficiently when given for instance orally or nasally or by the rectal route. A drug formulation intended for parenteral use has to meet a number of requirements in order to be approved by the regulatory authorities for use in humans. Thus, it has to be biocompatible and biodegradable and all substances used and their degradation products should be non toxic. In addition thereto, particulate drugs intended for injection have to be small enough to pass through the injection needle, which preferably means that they should be smaller than 200 µm. The drug should not be degraded to any large extent in the formulation during production or storage thereof or after administration and should be released in a biologically active form with reproducible kinetics.

One class of polymers which fulfils the requirements as to biocompatibility and biodegradation to harmless end products are the linear polyesters based on lactic acid, glycolic acid and mixtures thereof. In the text below said polymers will also be referred to as PLGA. PLGA is degraded by ester hydrolysis to lactic acid and glycolic acid and has been shown to display excellent biocompatiblity. The innocous nature of PLGA is furthermore exemplified by the approval of several parenteral sustained release formulations based on these polymers by regulatory authorities, like the US Food and Drug Administration.

Parenterally administrable sustained release products on the market today based on PLGA include Decapeptyl™ (Ibsen Biotech), Prostap SRυ (Lederle), Decapeptyl® Depot (Ferring) och Zoladex® (Zeneca). The drugs of these formulations are all peptides. In other words they consist of amino acids condensed to a polymer with a relatively low degree of polymerisation and they do not have any well defined three-dimensional structure. This in turn generally permits the use of rather harsh conditions during preparations of said products. For example extrusion and subsequent size reduction can be used, which techniques should not be permissible in connection with proteins since they generally do not withstand such harsh conditions.

Consequently there is also a need for sustained release formulations for proteins. Proteins are similar to peptides in that they also consist of amino acids, but the molecules are larger and most proteins are dependant on a well defined three-dimensional structure as to many of their properties, including biological activities and immunogenicity. Their three-dimensional structures can relatively easily be destroyed, for example by high temperatures, surface induced denaturation and, in many cases exposure to organic solvents. Thus, a very serious drawback in connection with the use of PLGA, which is an excellent material per se, for sustained release of proteins is the requirement to utilize organic solvents to dissolve said PLGA, with the associated risk of compromising the stability of the protein.

Despite large efforts aiming at a modification of the PLGA technology in order to avoid this inherent problem with protein instability during the preparation process the progress in this field has been very slow and as yet no protein products have appeared on the market based on PLGA technology. The main reason therefore probably is that the three-dimensional structures of most proteins are too sensitive to withstand the preparation procedures used and/or being stored in a PLGA-matrix.

The most commonly used technique at present for entrapping water soluble substances such as proteins and peptides is the use of multiple emulsion systems. The drug substance is dissolved in a water or buffer solution and then mixed with an organic solvent, immiscible with water, containing the dissolved polymer. An emulsion is created having the water phase as the inner phase. Different types of emulsifiers and vigorous mixing are often used to create this first emulsion. Said emulsion is then transferred, under stirring, to another liquid, typically water, containing another polymer, for example polyvinylalalcohol, giving a triple w/o/w-emulsion. The microspheres are then hardened in some way. The most commonly used way is to utilize an organic solvent having a low boiling point, typically dichloromethane, and to evaporate the solvent. If the organic solvent is not fully immiscible with water, a continuous extraction procedure can be used by adding more water to the triple emulsion. A number of variations of this general procedure are also described in the literature. In some cases the primary emulsion is mixed with a non-aqueous phase, for instance silicon oil. Solid drug materials rather than dissolved drugs can also be used.

The release profiles of proteins from microspheres prepared by said method often show a fast initial release followed by a slower phase. Said slower phase can be followed by a third phase of faster release.

PLGA microspheres containing proteins are disclosed in WO-A1-9013780, the main feature of which is the use of very low temperatures during the manufacture of the microspheres in order to retain high biological activity of the proteins. The activity of encapsulated superoxide dismutase was measured but merely on the portion released from the particles. This method has been used to produce PLGA microspheres containing human growth hormone in WO-A1-9412158 by dispersing human growth hormone in methylene chloride containing PLGA, spraying the obtained dispersion into a container with frozen ethanol with a layer of liquid nitrogen thereabove in order to freeze the droplets and allow them to settle in the nitrogen on to the ethanol. The ethanol is then thawed and the microspheres start to sink in the ethanol where the methylene chloride is extracted into the ethanol and the microspheres are hardened. This approach may be able to retain the stability of proteins better than most other processes for entrapping proteins in PLGA microspheres. However, this still remains to be unequivocally demonstrated for other proteins.

However, in the earlier mentioned methods based on encapsulation with PLGA the active substances are subjected to an organic solvent and this is generally detrimental to the stability of a protein. In addition thereto, the emulsion processes referred to above are complicated and likely to be problematic to scale up to an industrial scale. Furthermore, many of the organic solvents used in many of these processes are fraught with environmental problems and their high affinities for the PLGA polymer make removal difficult.

A parenterally administrable sustained release formulation should be able to control the release of the entrapped drug in an accurate way. In many of the systems based on PLGA the release of the active ingredient is largely dependent on the amount of drug substance incorporated into the microparticle, due to the formation of channels in the microparticles at higher drug loadings. This also contributes to a high initial burst at high drug loading.

A well known way of controlling the release of small molecules from a solid core is to apply a coating that produces a rate controlling film on the surface of the core. This is a general method of controlling the release rate of drugs to be administered by the oral route. One way of applying similar coats is by the use of air suspension technology. However, in connection with coating particles for use in parenteral administration, which particles are generally of a size below 200 $\mu$m, and often smaller, generally severe problems are encountered. Such problems can be an increased tendency for particles to agglomerate and problems with static electricity disturbing the manufacturing process.

Some different ways of coating particles of such small sizes are dispersion of the drug in a solution of the coating material and subsequent spray drying and a number of coacervation methods where a dissolved polymer is used to encapsulate the core material in different ways. However, all these methods would expose a protein to the organic solvent used to dissolve the PLGA. A method where a fluidized bed is used in the coating of microparticles is disclosed in U.S. Pat. No. 4,568,559. Here a solid, dry composite admixture is prepared from a uniform dispersion of an active ingredient of a film-forming polymer, the admixture then being ground and the resulting particles being sieved to obtain a size distribution of 1–150 $\mu$m. The core particles are then coated in a fluidized bed, a prerequisite, however, being that the same, or substantially the same, film-forming polymer material is used both for the preparation of the composite core and the coating to provide for bonding of the wall coating of the film-forming polymer to the core material. Thus, this method does not either eliminate the problem of exposing the protein to organic solvents if the film-forming polymer is PLGA or any other polymer that is not water soluble.

Thus, a method of producing parenterally administrable sustained release formulations for sensitive substances, for instance proteins, with the following properties would be highly desirable:

that can control the release rate of the entrapped substances within wide margins, typically from one or a few days to at least around one month;

that enables the production to be carried out with standard pharmaceutical equipment and which can be used from small scale manufacture to full scale production;

that makes it possible to eliminate, or minimise, the exposure of the active ingredient to organic solvents; and that is completely biodegradable and has a surface of a biocompatible material.

DESCRIPTION OF THE INVENTION

According to the present invention it has been found possible to prepare a parenterally administrable sustained release formulation with the characteristics referred to above. The new method claimed thus makes it possible to take advantage of the excellent biocompatibility and release controlling properties of PLGA while avoiding or minimising the exposure of for instance a protein to be formulated to organic solvents. However, the invention is not restricted to the use of PLGA only as a coating material or the use of a protein only as the active ingredient. Rather the invention is applicable to the use of any polymer that is film-forming, biodegradable and release-controlling, especially a polymer for which organic solvents have hitherto been utilized. Another prerequisite for a polymer is of course that it is pharmaceutically acceptable, which requirement is applicable also to all other materials or ingredients used in the formulation. Furthermore, the invention is useful for all active substances which may be utilized in parenteral administration. Primarily, however, the invention presents a solution to the previously described problem with active substances sensitive to or instable in organic solvents.

Briefly the invention is based on the idea on entrapping the active ingredient in microparticles without using any organic solvent, working up the microparticles to the dry state and subsequently coating the microparticles with a biodegradable polymer using an air suspension technique to remove, very rapidly, any organic solvent used for the polymer coating to avoid any substantial exposure of the active substance to organic solvent.

More specifically, according to a first aspect of the invention, a method is provided of preparing parenterally, preferably injectionally, administrable, sustained release microparticles containing a biologically active substance, especially a substance that is instable in the presence of an organic solvent, said method comprising preparing core particles from a biodegradable material in an aqeous medium that is essentially free from organic solvent, the biologically active substance being entrapped therein during or after said preparation, drying the core particles containing said active substance, optionally after a washing step to remove any excess of active substance, and coating the core particles with a film-forming, biodegradable, release-controlling polymer by air suspension technique so as to create a shell of said polymer on the core particles without any detrimental exposure of the active substance to organic solvent.

Since the method is primarily intended for the preparation of microparticles adapted for administration by injection, the microparticles preferably have an average diameter in the range of 10–200 $\mu$m. more preferably 20–100 $\mu$m. and most preferably smaller than 60 $\mu$m, e.g. 10–60 $\mu$m or 40–60 $\mu$m.

A preferable core particle material is a starch or a chemically or physically modified starch. Such materials are previously known per se in this technical field, and therefore reference can be made to the prior art concerning details about such starches. It can, however, be added that microparticles prepared from starch can be designed so as to be dissolved by $\alpha$-amylase, an enzyme present in serum and extracellular fluid, and as the end degradation product is glucose, starch microparticles can fulfil the requirement of biodegradability.

The preferred polymers for the shell are alifatic polyesters (e.g. homopolymers) or copolymers from ($\alpha$-hydroxy acids or cyclic dimers of $\alpha$-hydroxy acids.

Said $\alpha$-hydroxy acid is preferably selected from the group consisting of lactic acid and glycolic acid. In other words a preferred homopolymer can be for instance polylactic acid or polyglycolic acid, while a preferred copolymer can be a lactic acid/glycolic acid copolymer.

The cyclic dimers are preferably selected from the group consisting of glycolides and lactides.

However, as indicated above, other biodegradable polymers could also be used provided the polymer is able to form a film with the desired properties as to mechanical stability and release controlling properties, such as permeability to the active ingredient or the formation of pores. These properties could be fulfilled by the polymer itself or by including other substances in the coating. The coating material used could of course also be a mixture of two or more of the polymers referred to. Furthermore, said polymers may also be used in the form of their salts.

The biologically active substance can be entrapped in the microparticles without any use of organic solvent in several ways. An especially preferred way is the use of a so called aqueous two phase system technique, which is previously known per se. Said method is for instance disclosed in U.S. Pat. No. 4,822,535, which means that details about said technique can be found therein. Another way involves the preparation of core microparticles which are able to absorb water in a separate process, removal of any organic solvent used and loading the obtained microparticles with the active substance by exposing the dry microparticles to a solution of said active substance to have the solution absorbed by the microparticles, which are subsequently dried.

The drying of the core particles can be accomplished by any appropriate means, for example by spray drying, freeze drying or vacuum drying. In order to remove excess of active substance the microparticles or cores could also be washed prior to the drying step.

The core particles containing the active substance are subsequently coated by an air suspension technique which enables the creation of a shell of the polymer on the core particles without any substantial or detrimental exposure of the active substance to organic solvent. Said air suspension technique can be any method that is classified as an air suspension method and is able to apply a satisfactory coating. Preferred examples of such methods are methods wherein a fluidized bed or a so called spouted bed are utilized or the so called Wurster process, which method are all previously known per se and need not be described in detail here. Thus, the term "air suspension method" as used herein means any method where solid particles are suspended in an upwardly moving stream of gas. Said gas could be any gas capable of evaporating the solvent used and need not necessarily be air in spite of the term "air" suspension.

However, in connection with the air suspension technique it has been found that the problems with sensitive active substances and their exposures to organic solvents are eliminated, or essentially reduced, while preferably using a high flow rate of the air, or gas, sufficient to accomplish the desired result.

According to a preferable embodiment of the method claimed the polymer is applied on to the core particles from a solution, a pseudolatex or an emulsion thereof. In this connection it should be noted that an organic solvent can be utilized as the solvent for the polymer, as it has unexpectedly been found that by the new method according to the invention the active substance is not influenced to any substantial extent by the presence of such a solvent.

However, another preferable embodiment of the invention is represented by the case where said coating solution contains water, said pseudolatex is a pseudolatex of the polymer in water and said emulsion is an emulsion where one of the phases is a water phase. In the case of a mixture of different polymers, they can be present in different phases of an emulsion. Thus, it has been found that the presence of water can eliminate, or substantially reduce, the build up of static electricity during the coating procedure, and an especially preferred embodiment in this respect is the use of an emulsion where one of the phases is a liquid of the polymer in a solvent for said polymer and the other phase is water.

Last-mentioned emulsion is furthermore useful in a more general aspect, as will be described more specifically below and which also represents another aspect of the invention.

Another preferable embodiment of the invention is represented by the case wherein one or more stabilizing agents are incorporated in the particles during the preparation thereof. The nature of such a stabilizing agent is of course dependent on the specific active substance to be stabilized and said agent is chosen in line with known principles.

Additives can also be incorporated into the release-controlling polymer shell during the application thereof. Preferable examples of such additives are :film property modifying agents and release controlling agents. Examples as to the first category are plasticizers, e.g. triethyl-citrate, triacetin, polyethyleneglycol, polyethyleneoxide etc, while release controlling agents can be for instance inorganic bases (e.g. sodium hydroxide, potassium hydroxide, sodium carbonate, potassium carbonate, etc), organic bases (e.g. ethanol amine, diethanole amine, triethanole amine, lidocaine, tetracaine, etc,), inorganic acids (e.g. ammoniumsulfate, ammonium chloride, etc), organic acids (e.g. citric acid, lactic acid, glycolic acid, ascorbic acid, etc), and solid soluble substances which upon release create pores in the coating (e.g. crystals of sodium chloride, glucose, mannitol, sucrose, etc).

Additives to be included in the case where an emulsion or a pseudolatex is created are for instance emulsifiers.

The required amount of coating material depends on for example the size of the microcapsules, the composition of the coating and the desired release characteristics. Typical amounts are, however, 1–200 percent by weight, preferably 5–100 percent by weight, based on the weight of the core.

After the application of the coating controlling the release of the entrapped active substance additional materials could also be applied, e.g. sprayed, on to the microparticles in order to further modify the properties thereof or to facilitate the handling thereof. Examples of such materials are mannitol, sucrose and sodium chloride.

As already indicated above the invention is especially interesting in connection with proteins, peptides and polypeptides or other drugs or biologically active substances which are sensitive to or instable in the presence of organic solvents. However, generally the invention is not limited to the presence of such substances only as the inventive idea is applicable to any biologically active substance which can be used for parenteral administration. Thus, in addition to sensitive or instability problems the invention may well be of special interest in cases where it would otherwise be difficult to remove solvents or where toxicological or other environmental problems might occur.

According to a second aspect of the invention there is also provided parenterally administrable sustained release microparticles per se, which comprise a) core particles of a biodegradable material with the active substance entrapped therein, which core particles have been prepared in an aqueous medium essentially free from organic solvent, and b) a shell of a film-forming, biodegradable, release-controlling polymer on said core particles, which shell has been applied on said core particles by air suspension technique.

As to preferable embodiments and examples of materials and techniques to be used in connection therewith, reference is made to all embodiments and examples specified above and which will not be repeated once more.

According to a third aspect of the invention there is also provided a method of coating small particles in general, preferably microparticles as defined above, by air suspension technique, which method comprises applying on said particles, by air suspension technique, a coating emulsion of a coating material where one of the phases is a liquid of the coating material in a solvent and the other phase is water.

Thus, by such a method it has been found possible to eliminate or reduce problems associated with static electricity in air suspension coating of small particles.

The background of this aspect of the invention is as follows. The technology of air suspension coating of tablets, granules and small particles is well known. When the coating is made with the coating material in an organic solvent static electricity can be a problem. This problem is more pronounced when coating small particles. Thus, small particles have a tendency of adhearing to the walls of the coating chamber and also to each other, making the problem with unwanted agglomeration more severe. Particles sticking to the wall of the coating apparatus can cause uneven coating in the batch, lower yield and a less controllable process.

For some coating polymers the use of an aqueous disersion of latex or pseudolatex eliminates or reduces the problems associated with static electricity. It has not been possible to use a latex dispersion for all coating polymers with the same quality of the film being obtained from organic solvent based system. This aspect of the invention makes it possible to circumvent this problem.

In this context it should be added that the particles in connection with the invention are not specifically limited as to size or composition. Thus, it may be a drug substance or particles containing drug substances, fertilizers, etc.

The coating material is any coating material, e.g. a film-forming polymer, which could be used in air suspension coating and which is soluble in a solvent not totally miscible with water. Examples of coating materials are the polymers specifically referred to above. Examples of appropriate solvents are higher alcohols, esters, ethers, ketones, chlorinated hydrocarbons, aliphatic hydrocarbons and aromatic hydrocarbons.

The coating emulsion is made by mixing an aqueous phase with an organic phase. The coating material is dissolved in the organic phase. The emulsification step can be carried out by any of the conventional dispersing procedures, such as intermittent agitation, mixing with a propeller, turbine mixer or magnetic mixer, colloid mill process, homogenisation process or sonification process. The organic phase can be either the internal or the external phase.

An emulsifier may be added to stabilise the emulsion. Preferable examples thereof are anionic surfactants or non-ionic surfactants. These emulsifiers can be used alone or in combination.

The coating equipment used according to this aspect of the invention, as well as in connection with the first aspect of the invention, could be any type of air suspension equipment capable of coating particles, especially small particles.

EXAMPLES

The invention will now be exemplified by the following non-limiting examples wherein microparticles containing BSA, which is the most extensively used model protein for systems like this due to its well known characteristics and moderate cost, are coated with a layer comprising poly (lactide-co-glycolide). Furthermore, microparticles containing human insulin are coated, since insulin is known to be a sensitive protein and the biological activity of the final preparation can easily by assayed in vivo. The microparticles are prepared for example in accordance with technique disclosed in U.S. Pat. No. 4, 822,535. The coating is applied with commersially available equipment and the parameters set in the examples should merely be regarded as guidelines, since adjustments may be needed in many cases in order to obtain optimal conditions for the coating.

Procedure for Preparing the Core Particles

Example 1

Two-phase immobilisation in accordance with U.S. Pat. No. 4,822,535.

1. Weigh out 80 g of starch (Amioca 50, National Starch) and suspend in 320 g of 50 mM sodium bicarbonate buffer pH 9,8.
2. Heat the suspension until the starch has been totally dissolved.
3. Cool the solution to 50° C.
4. Add 96 ml of a 9,26% BSA solution (room temperature) in 50 mM sodium bicarbonate buffer pH 9,8 and stir for 10 seconds.
5. Add starch-protein solution to 800 ml of a 20 w/w % polyethylene glycol solution in 50 mM sodium bicarbonate buffer pH 9,8 (room temperature, Av. Mol. Wt. 20000), under continous stirring.
6. After 2 minutes,. add 3200 ml of a 40 w/w % polyethylene glycol solution in 50 mM sodium bicarbonate buffer pH 9,8 (room temperature, Av. Mol. Wt. 20000), under continous stirring.
7. Stir for 24 h.
8. The obtained microparticles are washed and vaccum dried.
9. The dry microparticles are sieved through a 160 $\mu$m mesh.

Example 2

1. Weigh out 80 g of starch (Amioca 50, National Starch) and suspend in 420 g of water.
2. Heat the suspension until the starch has been totally dissolved.
3. Cool the solution to 50° C.
4. Add the starch solution to 800 ml of a 20 w/w % polyethylene glycol solution in water (room temperature, Av. Mol. Wt. 20000 D), under continous stirring.
5. After 2 minutes, add 3200 ml of a 40 w/w % polyethylene glycol solution in water (room temperature, Av. Mol. Wt. 20000 D), under continous stirring.
6. Stir for 24 h.
7. The obtained microparticles are washed and vacuum dried.
8. The dried microparticles are impregnated with a 5% (w/w) BSA solution in water. Equal weight of particles and BSA-solution are used.
9. After 3 h the particles are freeze dried.
10. The dried microspheres are sieved through a 160 $\mu$m sieve.

PROCEDURE FOR PREPARING THE CORE PARTICLES

Example 3

1. Weigh out 80 g of starch (Amioca 50, National Starch) and suspend in 320 g of 50 mM sodium bicarbonate buffer pH 9,8.

2. Heat the suspension until the starch has been totally dissolved.
3. Cool the solution to 50° C.
4. Centrifuge 2511 ml of Monotard® from Novo Nordisk corresponding to 8.89 g insulin. Wash the insulin once with 500 ml of a buffer containing 0.15 M NaCl, 1 mM $ZnCl_2$ and 10 mM Sodium acetate with a pH of 7.3 and centrifuge again. Mix the insulin with the starch solution and stir for 10 seconds.
5. Add starch-protein solution to 800 ml of a 20 w/w % polyethylene glycol solution in 50 mM sodium bicarbonate buffer pH 9,8 (room temperature, Av. Mol. Wt. 20000), under continous stirring.
6. After 2 minutes, add 3200 ml of a 40 w/w % polyethylene glycol solution in 50 mM sodium bicarbonate buffer pH 9,8 (room temperature, Av. Mol. Wt. 20000), under continous stirring.
7. Stir for 24 h.
8. The obtained microparticles are washed and vaccum dried.

Procedure for Preparing the Shell

Example 4

Procedure for Preparing the Coating Solution

1. Weigh out 200 g of poly(lactide-co-glycolide 75/25) Resomer RG756 from Boeringer Ingelheim.
2. Add 10 g of triacetin.
3. Dissolve it in 3123 g of acetone.

Procedure for Applying the Coating 1. 500 g of starch microparticles containing 3,5% BSA are loaded in a Glatt GPCG 6" Wurster.
2. The following conditions of the Wurster are set:

| | |
|---|---|
| Atomization pressure | 3 bar |
| Atomizing nozzle | 0.8 mm |
| Inlet temperature | 38–40° C. |
| Outlet temperature | 33–37° C. |
| Product temperature | 34–38° C. |
| Air velocity | 3.2–3.4 m/s |
| Flow of coating solution | 4.4 ml/min |

Example 5

Procedure for Preparing the Coating Solution

1. Weigh out 200 g of poly(lactide-co-glycolide 50/50) Resomer RG504H from Boeringer Ingelheim.
2. Dissolve it in 3133 g of acetone.

Procedure for Applying the Coating 1. 500 g of starch microparticles containing 3,5% BSA are loaded in a Glatt GPCG 6" Wurster.
2. The following conditions of the Wurster are set:

| | |
|---|---|
| Atomization pressure | 3 bar |
| Atomizing nozzle | 0.8 mm |
| Inlet temperature | 38–40° C. |
| Outlet temperature | 33–37° C. |
| Product temperature | 34–38° C. |
| Air velocity | 3.0–3.2 m/s |
| Flow of coating solution | 4.4 ml/min |

3. Recover the coated product

Example 6

Procedure for Preparing the Coating Solution

1. Weigh out 40 g of poly(D,L lactide) Resomer R104 and 40 g of poly(lactide-co-glycolide 75/25) Resomer RG756 from Boeringer Ingelheim.
2. Dissolve it in 1252 g of ethyl acetate.
3. Mix 2504 g of water with 1,6 g of Tween 80.
4. Mix the polymer solution and the water solution using an Ystral turrax mixer at high speed.

Procedure for Applying the Coating 1. 100 g of starch microparticles containing 2,7% BSA are loaded in a Huttlin Kugelcoater HKC005.
2. The following conditions for the kugelcoater are set:

| | |
|---|---|
| Atomization pressure | 0.8 bar |
| Microclimate pressure | 0.4 bar |
| Atomizing nozzle | 0.6 mm |
| Inlet temperature | 25–27° C. |
| Outlet temperature | 20–24° C. |
| Flow of coating solution | 5–7 g/min |

3. After coating with PLGA, 200 g of a water solution containing 10 w/w % mannitol and 0,4 w/w % Tween 80 are sprayed onto the particles with a flow of 3,5 g/min.
4. Recover the coated product.

Method for in Vitro Release

The in vitro release is monitored by weighing up 70 mg of coated product and adding 1,5 ml of buffer solution to a polypropylene eppendorf tube. The release buffer consists of sodium phosphate 30 mM, pH 7,4, I-0,154 with sodium chloride, 1 mM calcium chloride, α-amylase 72 U/l, and sodium azide 0,02%. At proper intervals 1 ml of buffer is removed and fresh buffer is added to the samples in order to maintain the correct pH. The tubes are slowly rocked in 37° C. The protein and starch concentrations are measured together with pH.

Method for in vivo Release

10 SPF female rats (9–10 weeks, 170–180 g) were used for studying the in vivo release of BSA from the coated microspheres. 200 µl of a suspension containing 163 mg/ml of microparticles prepared according to example 6 were injected subcutaneously in the neck. The vehicle for the injection was physiological sodium chloride solution containing 3% of sodium carboxymethylcellulose as suspension aid. The injection was made using a 21 G needle.

As a control group, non coated microspheres were given to 8 animals for comparison. The dose of BSA was four times higher in the coated preparation than in the non coated preparation.

Blood samples for measuring BSA were taken from the orbital plexus day 0 before dosing and in the afternoon, and at the same times of the day on day 1, 2, 3, 4, 5, 6 and 7. Five hundred µl of blood were taken and analysed for BSA in serum. The BSA concentrations in serum were analysed using an ELISA method based on a commercially available antibody (Dakopatts) reacting with bovine, but not rat, albumin.

Example 7

The procedure for preparing the coating solution was similar to that of Example 6.

Procedure for Applying the Coating 100 g of starch microparticles containing 9.3% of insulin (Monotard® from Novo Nordisk) are loaded in a Huttlin Kugelcoater HKC005.

The rest of the coating procedure is similar to that of Example 6.

Method for in Vivo Release

10 SPF female rats (9–10 weeks, 170–180 g) were used for studying the biological effects of the preparation of Example 7. Three days before injection with the test substance, the rats were treated with 65 mg/kg of streptozotocin in order to induce diabetes. Streptozotocin was dissolved in a 1% citrate buffer at pH 4.5 maximally two minutes before injection.

At the day of injection, 200 µl of a suspension contaning 51 mg/ml of the microparticles from Example 7 were injected subcutaneously in the neck. The vehicle for the injection was physiological sodium chloride solution containing 3% of sodium carboximethylcellulose as suspension aid. The injection was made using a 21 G needle. As a control group, non coated microsphehres were given to 8 animals for comparison. The insulin dose was 2.5 times higher for the non coated microspheres than for the coated microspheres.

Blood samples for measuring blood glucose were taken from the orbital plexus day 0 before insulin dosing and in the afternoon, and at the same times of the day on day 1, 2, 3, 4, 5, 6 and 7 and in the afternoon on day 9 and for the animals given coated microspheres also in the afternoon on day 11. Blood glucose analyses were performed using a commercial kit from Roche on a COBAS MIRA.

FIGURES

The protein releases from the in vitro tests and the BSA concentrations and blood glucose levels from the two in vivo tests are shown in the Figures of the accompanying drawings, wherein FIG. 1 shows the release from the coated particles of Example 4;

More specifically the following can be seen from the Figures.

Figure 1:
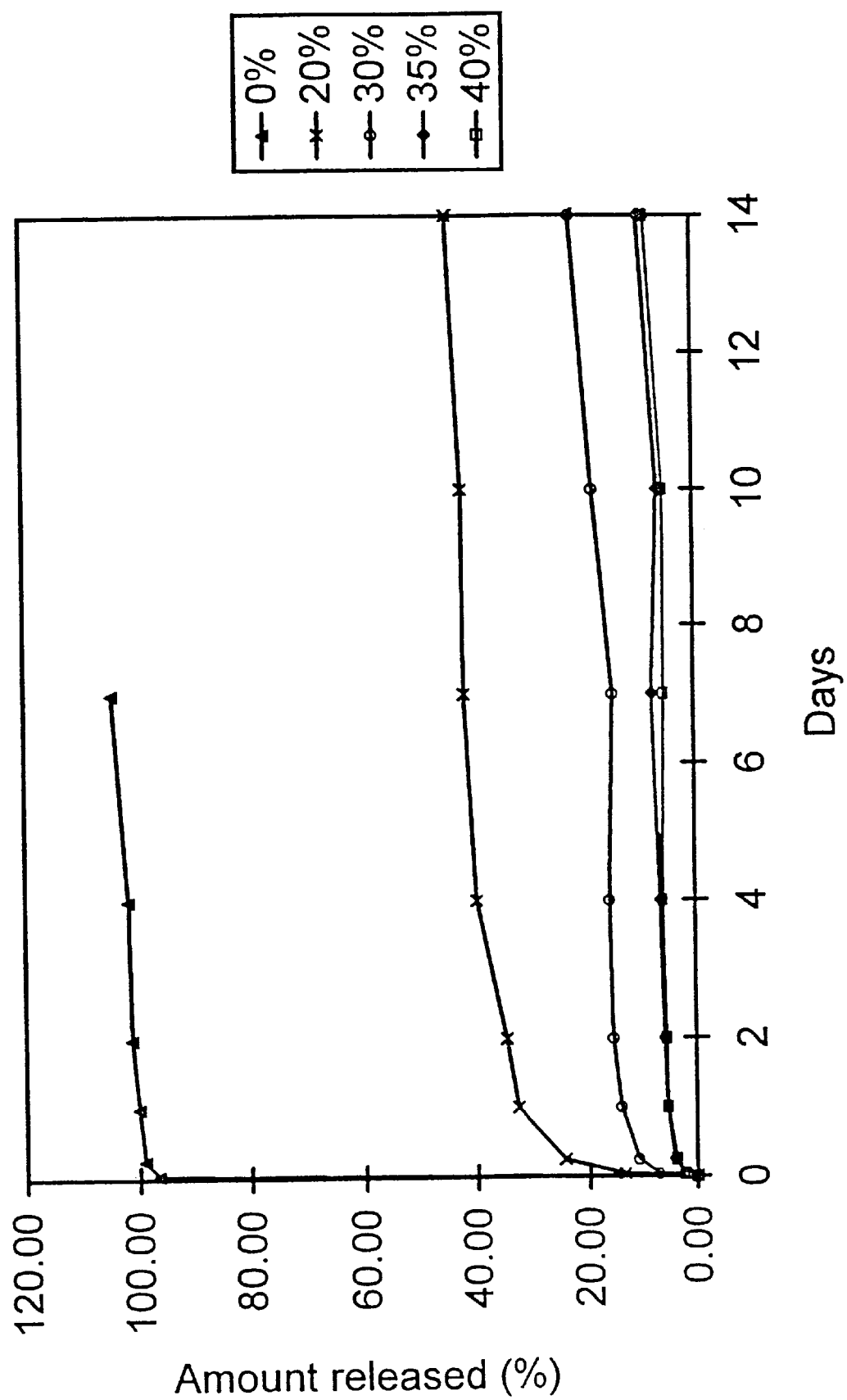

In FIG. 1, the cumulative protein release from the coated particles in Example 4 can be seen. The curves represent different coating levels (weight percent of coating polymer added based on the weight of the core) as indicated in the legend. The core degrades rapidly and releases most of the protein in a very short time. A burst can be seen at all coating levels but is decreased more and more. The coating polymer degrades slowly and therefore no appreciable amount of protein is released after the burst phase.

Figure 2:
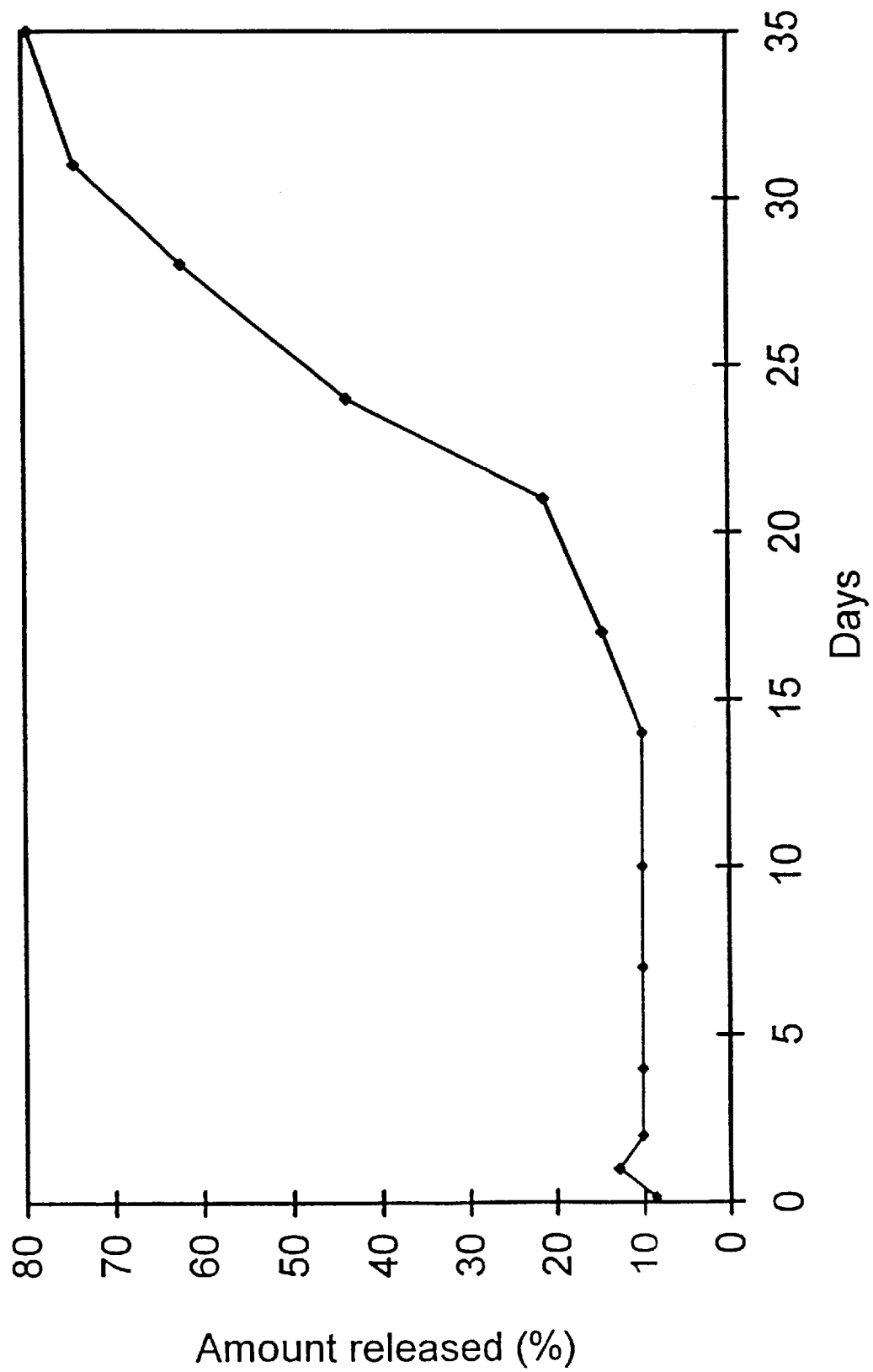
FIG. 2 shows the release from the coated particles of Example 5.

In FIG. 2, the protein release from the coated particles 40% coating level, as defined above in Example 5 is shown. The polymer is now more easily dreaded, giving first a limited burst similar to Example 4 but then after around 2 weeks, the rest of the protein begins to be relased from the coated microparticles.

Figure 3:
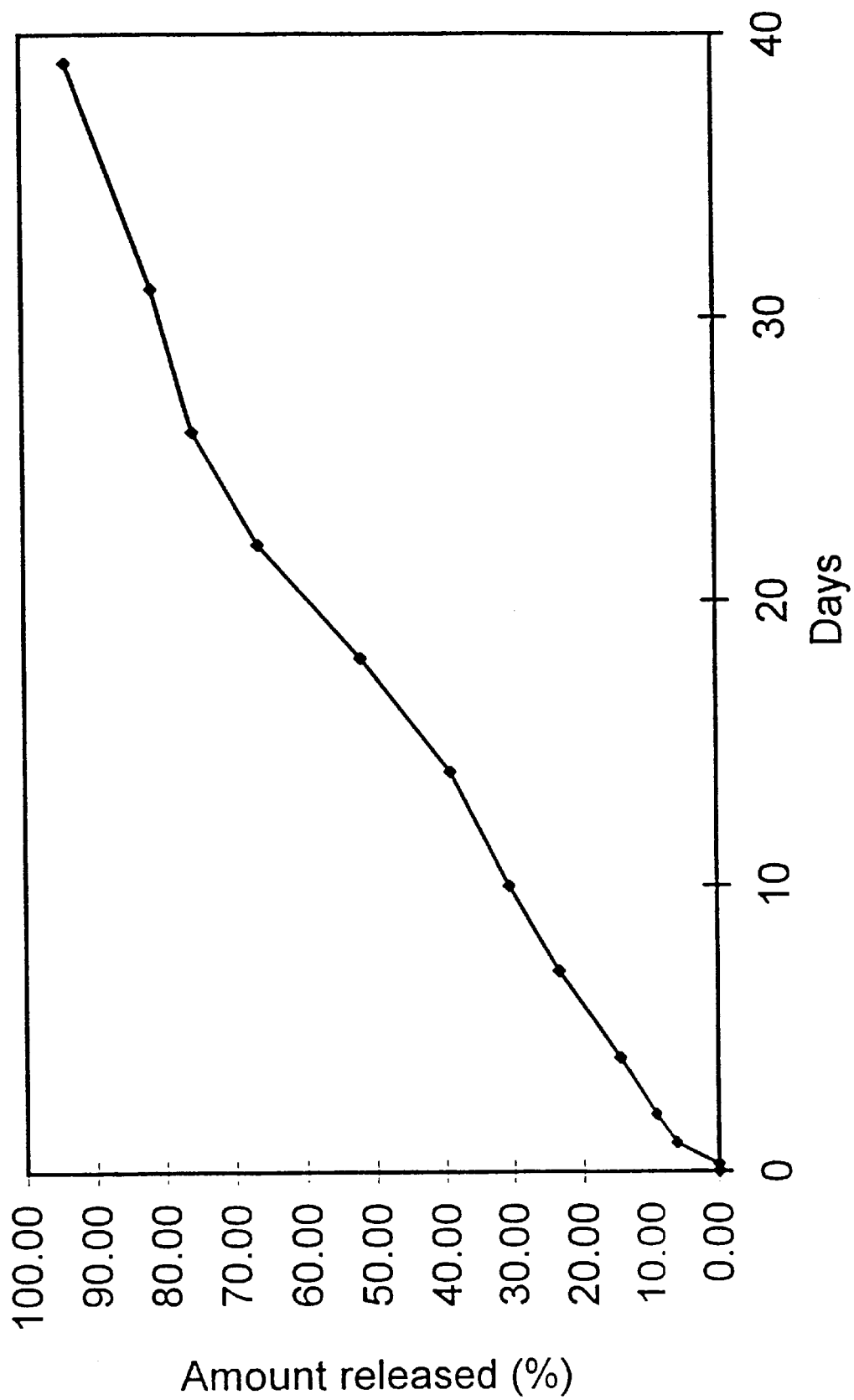
FIG. 3 shows the release from the coated particles of Example 6.

In FIG. 3, protein release from the coated particles (80% coating level, as defined above) from Example 6 can be seen. In this case, the protein is released more continously than from Example 4 and 5.

Figure 4:
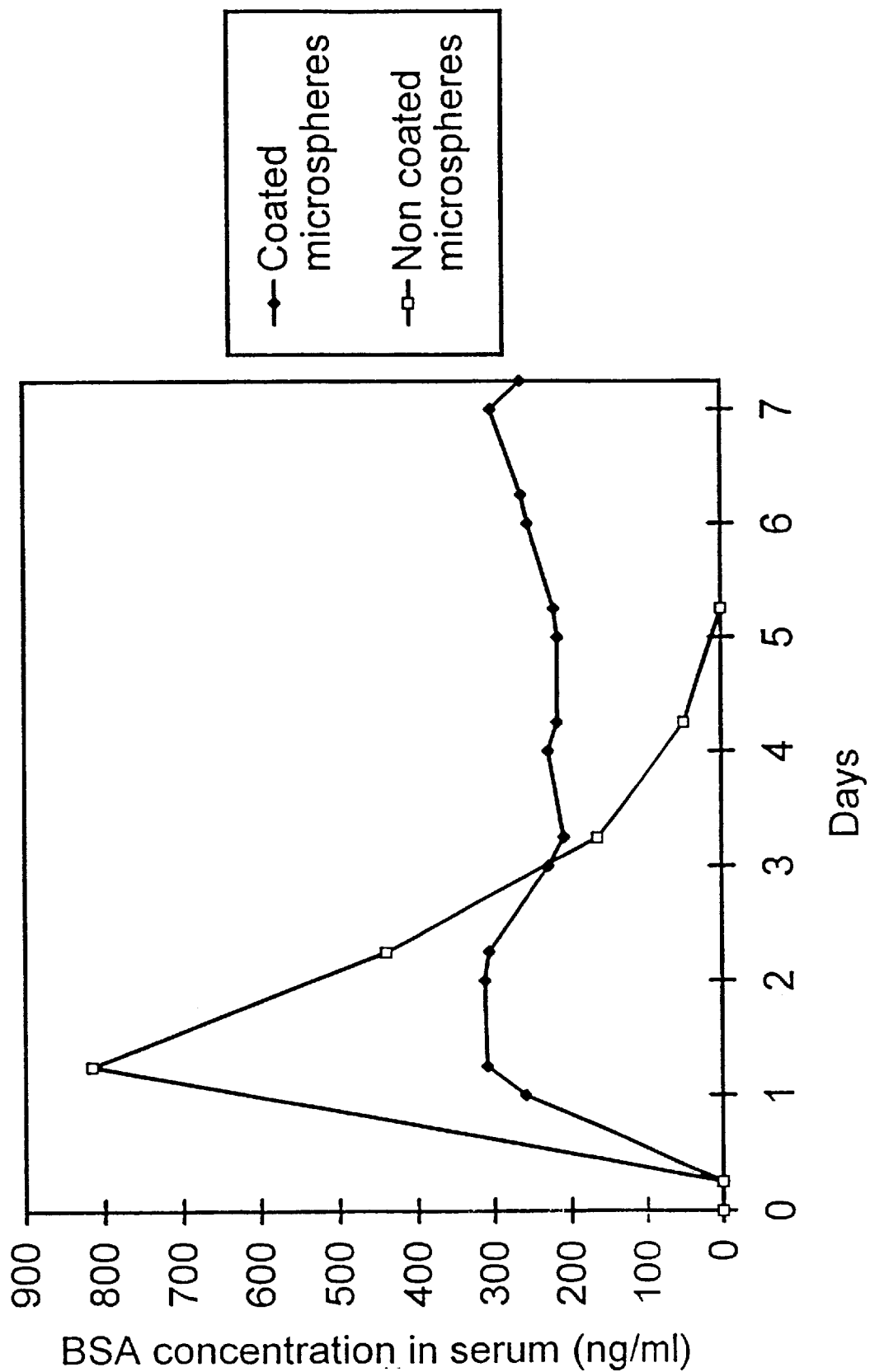
FIG. 4 shows the mean BSA concentrations in serum from the in vivo release for the coated particles of Example 6 and non coated BSA particles.

In FIG. 4, the mean BSA concentrations from the in vivo release can be seen. A steady release of BSA is shown during the whole study compared to the non coated microspheres.

Figure 5:
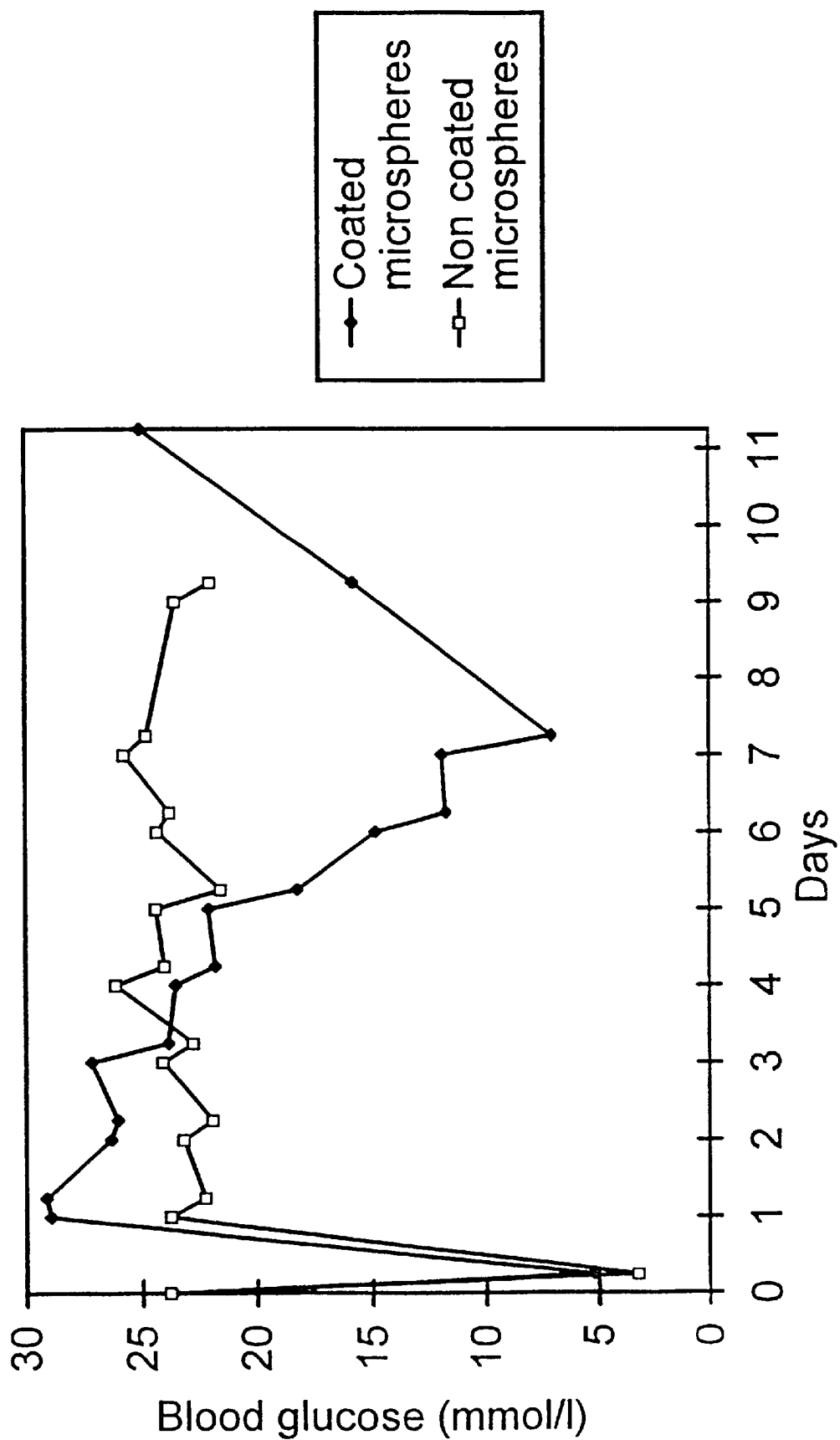
FIG. 5 shows the mean blood glucose levels from the in vivo release of insulin from the particles of Example 7 and non coated insulin particles.

In FIG. 5, the mean blood glucose levels from the in vivo release of insulin from the particles of Example 7 and non coated particles are shown. For both preparations, a fast normalisation of the blood glucose level after 6 hours can be seen. After one day, the levels are back to diabetic levels but for the coated preparation, the levels start to decrease again, showing a maximal depression of the blood glucose level after seven days. At day 11, the blood glucose levels are back again to the diabetic state. The insulin has thus retained its biological activity throughout the process and for at least 9 day after injection. For the non coated particles, no delayed effect could be seen.

What is claimed is:

1. A method for preparing parenterally administerable, sustained release microparticles containing a biologically active substance, which method comprises (i) preparing core particles from a biodegradable material in an aqueous medium which substantially lacks any organic solvents which are detrimental to the activity of said active substance; such that said biologically active substance becomes entrapped in said particles during or after said preparation; (ii) drying said core particles containing said active substance; and (iii) coating said core particles with a film-forming, biodegradable, release-controlling polymer by an air suspension technique which results in the creation of a shell comprised of said polymer containing said core particles under condition that avoid exposure of the active substance to any detrimental organic solvent potentially detrimental to the activity of said active substance.

2. The method of claim 1, which includes a washing step intervening steps (i) and (ii).

3. The method of claim 1, wherein said parenterally administrable microparticles are administrable via injection.

4. The method of claim 1, wherein said microparticles have a mean diameter ranging from 10 to 100 µm.

5. The method of claim 4, wherein said particles have a mean diameter ranging from 20 to 100 µm.

6. The method of claim 1, wherein said core particle material is selected from the group consisting of starches, and modified forms thereof.

7. The method of claim 1, wherein said polymer is selected from the group consisting of homo- or copolymers prepared from (α-hydroxy acids and/or cyclic dimers of α-hydroxy acids.

8. The method of claim 7, wherein said α-hydroxy acid is selected from the group consisting of lactic acid and glycolic acid.

9. The method according to claim 7, wherein said cyclic dimers are selected from the group consisting of glycolides and lactides.

10. The method of claim 1, wherein said core particles are prepared by a method comprising an aqueous two-phase system.

11. The method of claim 1, wherein said polymer is applied to the core particles in the form of a solution, a pseudolatex, or an emulsion.

12. The method according to claim 11, wherein said coating solution is an aqueous solution.

13. The method of claim 11, wherein said pseudolatex comprises an aqueous polymer composition.

14. The method of claim 11, wherein said emulsion is an aqueous emulsion.

15. The method of claim 14, wherein said emulsion comprises an aqueous emulsion wherein one of the phases comprises a polymer dissolved in a solvent.

16. The method according to claim 1, wherein said air suspension technique is selected from the group consisting of fluidized bed techniques, spouted bed techniques, and Wurster process techniques.

17. The method of claim 16, wherein said fluidized bed technique comprises a vacuum fluidized bed technique.

18. The method of claim 1, wherein said cores particles further comprise agents which stabilize the active substance contained therein.

19. The method according to claim 1, wherein at least one additional additive is incorporated into the release-controlling polymer shell during application thereof, and wherein said at least one additive is selected from the group consisting of film property modifying agents and release-controlling agents.

20. The method of claim 19, wherein said film property modifying agent is a plasticizer or surfactant.

21. The method according to claim 1, wherein the amount of said polymer shell material ranges from 1 to 200 percent by weight relative to the core weight.

22. The method according to claim 21, wherein the amount of the polymer shell material ranges from 5 to 100 percent by weight relative to the core weight.

23. A method according to claim 1, wherein said biologically active substance is a substance which is sensitive to exposure to organic solvents.

24. A method according to claim 1, wherein said active substance is selected from the group consisting of peptides, polypeptides, and proteins.

25. A method of coating small particles comprising applying to said small particles by an air suspension technique an emulsion comprising a polymeric coating material wherein one of the phases of said emulsion is a liquid of said polymeric coating material comprised in a solvent and the other phase is water.

26. The method of claim 25, wherein said small particles are microparticles.

27. Parenterally administrable sustained release microparticles, which comprise:
   (a) core particles of a biodegradable material and entrapped therein a biologically active substance which is sensitive to exposure to organic solvents, said core particles having been prepared in an aqueous medium essentially free from organic solvent to which said biologically active substance is sensitive; and
   (b) a shell, on said core particles, from a film-forming, biodegradable, release-controlling polymer; said shell having been applied on the core particles by means of air-suspension technique.

28. Microparticles of claim 27, wherein said biologically active substance is selected from the group consisting of peptides, polypeptides and proteins.

29. Microparticles of claim 27, which have a mean diameter ranging from 10 to 100 $\mu$m.

30. Microparticles of claim 27, wherein said core particle material is selected from the group consisting of starches and modified forms thereof.

31. Microparticles of claim 27, wherein said shell-forming polymer is selected from the group consisting of homo- or copolymers prepared from α-hydroxy acids and/or cyclic dimers or α-hydroxy acids.

32. Microparticles of claim 27, wherein said shell-forming polymer has been applied to the core particles in the form of an aqueous emulsion thereof.

* * * * *